(12) United States Patent
Perrault, Jr.

(10) Patent No.: US 9,529,203 B2
(45) Date of Patent: Dec. 27, 2016

(54) FOCAL PLANE SHIFTING SYSTEM

(71) Applicant: CYTONOME/ST, LLC, Boston, MA (US)

(72) Inventor: Donald Francis Perrault, Jr., Brighton, MA (US)

(73) Assignee: CYTONOME/ST, LLC, Boston, MA (US)

( * ) Notice: Subject to any disclaimer, the term of this patent is extended or adjusted under 35 U.S.C. 154(b) by 281 days.

(21) Appl. No.: 14/029,485

(22) Filed: Sep. 17, 2013

(65) Prior Publication Data

US 2014/0085898 A1 Mar. 27, 2014

Related U.S. Application Data

(60) Provisional application No. 61/702,114, filed on Sep. 17, 2012.

(51) Int. Cl.
| | | |
|---|---|---|
| *G02B 3/00* | (2006.01) | |
| *G02B 9/00* | (2006.01) | |
| *G02B 27/12* | (2006.01) | |
| *G02B 3/10* | (2006.01) | |
| *G01N 15/14* | (2006.01) | |
| *G01N 15/10* | (2006.01) | |
| *B01L 3/00* | (2006.01) | |

(52) U.S. Cl.
CPC ........... *G02B 27/12* (2013.01); *G01N 15/1434* (2013.01); *G01N 15/1459* (2013.01); *G01N 15/1484* (2013.01); *G02B 3/10* (2013.01); *B01L 3/502715* (2013.01); *G01N 2015/1006* (2013.01); *G01N 2015/149* (2013.01)

(58) Field of Classification Search
CPC . G11B 7/1353; G02B 3/0087; G02B 27/0037; G02B 27/0944
USPC .................................................. 359/652–655
See application file for complete search history.

(56) References Cited

U.S. PATENT DOCUMENTS

| | | | |
|---|---|---|---|
| 6,372,506 B1 | 4/2002 | Norton | |
| 6,808,075 B2 | 10/2004 | Bohm et al. | |
| 6,976,590 B2 | 12/2005 | Deshpande et al. | |
| 7,179,423 B2 | 2/2007 | Bohm et al. | |
| 7,211,442 B2 | 5/2007 | Gilbert et al. | |
| 7,298,478 B2 | 11/2007 | Gilbert et al. | |
| 7,646,544 B2 * | 1/2010 | Batchko et al. | ............. 359/665 |
| 8,277,764 B2 | 10/2012 | Gilbert et al. | |
| 2001/0026357 A1* | 10/2001 | Ota et al. | ........................ 355/53 |

(Continued)

FOREIGN PATENT DOCUMENTS

WO 2012/106294 A1 8/2012

*Primary Examiner* — Mahidere Sahle
(74) *Attorney, Agent, or Firm* — McCarter & English, LLP; David R. Burns

(57) ABSTRACT

Focal plane shift elements and optical systems with focal plane shifting features for illuminating flow-paths in a fluidic processing system are disclosed. An optical system may include a light source providing an incident first light beam. The optical system may include at least one optical element configured to collect and focus the incident first light beam to produce a second light beam having different portions simultaneously focused at two or more different locations along an optical path, with each location corresponding to a different flow-path of the fluidic processing system. The focal plane shift elements and optical systems with focal plane shifting features may be particularly useful in a microfluidic system.

22 Claims, 8 Drawing Sheets

(56) References Cited

U.S. PATENT DOCUMENTS

| | | |
|---|---|---|
| 2002/0197733 A1 | 12/2002 | Bohm et al. |
| 2003/0015425 A1 | 1/2003 | Bohm et al. |
| 2012/0177902 A1 | 7/2012 | Driscoll et al. |
| 2013/0006056 A1* | 1/2013 | Webb ................. A61B 1/00188 600/162 |

* cited by examiner

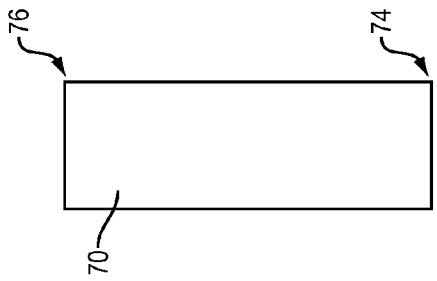
FIG. 12
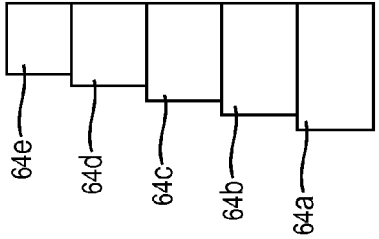
FIG. 11
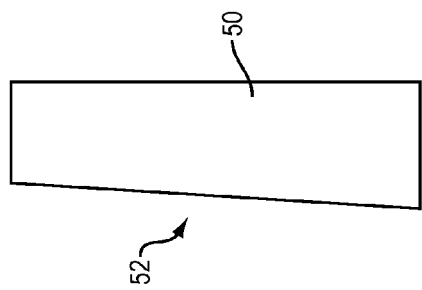
FIG. 8
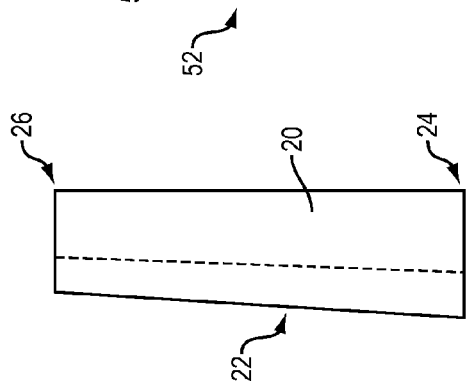
FIG. 7
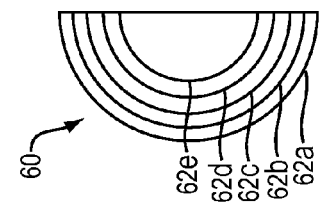
FIG. 10
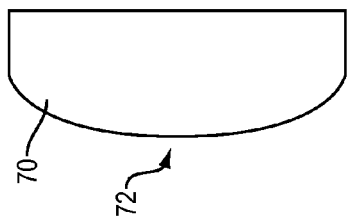
FIG. 6
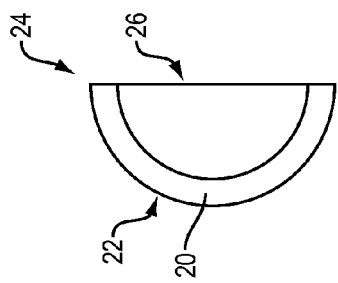
FIG. 9
FIG. 5

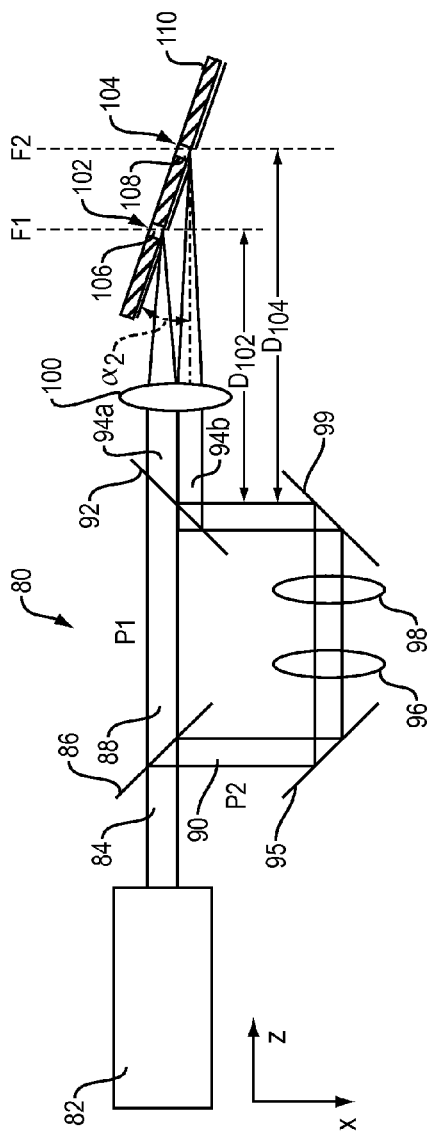
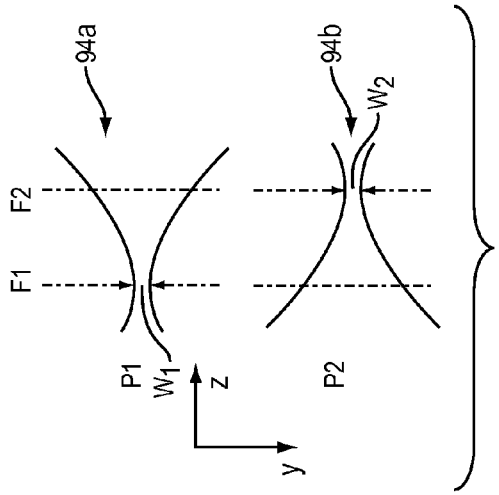
FIG. 13
FIG. 14

FOCAL PLANE SHIFTING SYSTEM

CROSS-REFERENCE TO RELATED APPLICATIONS

This application claims the benefit of and priority to U.S. Provisional Application No. 61/702,114 filed Sep. 17, 2012, the disclosure of which is incorporated by reference in its entirety.

TECHNICAL FIELD

The present invention generally relates to optical elements and optical systems for collecting and focusing light beams, and more particularly to optical elements and optical systems for collecting and focusing light beams for use with fluidic processing systems such as flow cytometers.

BACKGROUND

In the fields of biology and medicine, there is often a need for high throughput analysis and sorting of particles.

One well known technique for analyzing and sorting particles is droplet deflection. See, for example, U.S. Pat. No. 6,372,506, which is incorporated by reference, herein, in its entirety. In droplet deflection, a stream of suspended particles is broken into individual droplets, for example, using a piezoelectric mechanism. At the point of droplet formation, an electrical charging element is used to selectively charge each droplet. The charged droplet then free falls through an electrostatic field, which deflects the charged droplet into one of a plurality of receiving containers.

Another technique for analyzing and sorting particles involves utilizing switching or pressure mechanisms to divert a volume of fluid containing a particle into a selected branch channel of a flow-path defined on a microfluidic chip. See, for example, U.S. Pat. No. 6,808,075, which is incorporated by reference, herein, in its entirety.

In a microfluidic system, such as a droplet sorter or a microfluidic chip, an optical system may be used for monitoring, analyzing and/or detecting particles and/or liquids flowing through the system, for example, in a flow-path such as defined by a microchannel or by stream of droplets. Such an optical system for illuminating a flow-path of a microfluidic system may be useful, for example, in a particle sorting system that sorts particles based on one or more particle characteristics as detected using the optical system.

SUMMARY

Exemplary embodiments of optical elements, optical systems and fluidic processing systems incorporating the optical elements and/or systems are described herein and summarized below. These exemplary embodiments are not intended to limit the scope of the claimed invention which may encompass a variety of forms that may differ from these summaries.

According to certain aspects, embodiments include a focal plane shift element and an optical system for illuminating a plurality of flow-paths in a fluidic processing system.

An embodiment includes a focal plane shift element including an optical element configured to collect and focus an incident first light beam to produce a second light beam having different portions simultaneously focused at two or more different locations along an optical path.

In some embodiments, the focal plane shift element is configured to focus light incident on a first portion of the focal plane shift element at a first lateral position to form a first beam portion focused at a first location a first distance from the focal plane shift element, and configured to focus light incident on a second portion of the focal plane shift element at a second lateral position to form a second beam portion focused at a second location a second distance from the focal plane shift element.

In some embodiments, a distance between the focal plane shift element and a location of a focus of a beam portion formed from light incident on a portion of focal plane shift element located at a lateral position varies with the lateral position of the portion of the focal plane shift element.

In some embodiments, a distance between the focal plane shift element and a location of a focus of a beam portion formed from light incident on a portion of focal plane shift element located at a lateral position continuously varies with the lateral position of the portion of the focal plane shift element.

In some embodiments, the focal plane shift element is a refractive element. The focal plane shift element may have a laterally varying index of refraction. The focal plane shift element may include a surface having a laterally varying radius of curvature.

In some embodiments, the focal plane shift element is a diffractive element.

Another embodiment includes an optical system for illuminating a plurality of flow-paths in a fluidic processing system. The optical system includes, a light source providing an incident first light beam and at least one optical element configured to collect and focus the incident first light beam to produce a second light beam having different portions simultaneously focused at two or more different locations along an optical path.

In some embodiments, the at least one optical element includes a focal plane shift element configured to focus light incident on a first portion of the focal plane shift element at a first lateral position to form a first beam portion focused at a first location a first distance from the focal plane shift element thereby illuminating a first flow-path. The focal plane shift element is configured to focus light incident on a second portion of the focal plane shift element at a second lateral position to form a second beam portion focused at a second location a second distance from the focal plane shift element thereby illuminating a second flow-path. In some embodiments, the first location at least partially overlaps with the first flow-path and wherein the second location at least partially overlaps with the second flow-path. In some embodiments, the first location is near the first flow-path and the second location is near the second flow-path.

In some embodiments, the at least one optical element includes a beamsplitter configured to divide the incident first light beam into a first beam portion and a second beam portion. The at least one optical element also includes at least one second beam optical element set in a path of the second beam portion and a beam-combiner configured to combine the first beam portion and the second beam portion into a combined beam. The at least one optical element further includes a primary beam focusing element positioned before the beamsplitter or after the beam-combiner and configured to focus the first beam portion of the combined beam to a first location at a first optical path distance from the primary beam focusing element thereby illuminating a first flow-path, and configured to, in combination with the lens set, focus the second beam portion of the combined beam to a second location a second optical path distance from the primary beam focusing element thereby illuminating a second flow-path. The primary beam focusing element may be positioned in the optical path before the beamsplitter. The primary beam focusing element may be positioned in the optical path after the beam-combiner. In some embodiments, the optical system is configured such that the first beam portion of the combined beam is laterally offset from the second beam portion of the combined beam.

In some embodiments, each of the two or more different locations along the optical path corresponds to a different flow-path of the fluidic processing system.

An embodiment includes an optical system for illuminating flow-paths in a fluidic processing system. The optical system includes a light source providing an incident first light beam and at least one optical element configured to collect and focus the incident first light beam forming a second beam having beam waists located at two or more different distances along an optical path simultaneously.

In some embodiments, each beam waist is located at a different flow-path of the fluidic processing system.

Another embodiment includes an optical system for illuminating flow-paths in a fluidic processing system. The optical system includes a light source providing an incident light beam. And at least one optical element configured to collect and focus the incident light beam forming image planes located at two or more different distances along an optical path simultaneously.

In some embodiments, the at least one optical element comprises a focal plane shift element configured to focus light from a first portion of the focal plane shift element at a first lateral position forming a first image at a first distance from the focal plane shift element thereby illuminating a first flow-path. The focal plane shift element is also configured to focus light from a second portion of the focal plane shift element at a second lateral position forming a second image at a second distance from the focal plane shift element thereby illuminating a second flow-path.

In some embodiments, each image plane is located at a different flow-path of the fluidic processing system.

In some embodiments, each image plane is located near a different flow-path of the fluidic processing system.

The summary above is provided merely to introduce a selection of concepts that are further described below in the detailed description. The summary is not intended to identify key or essential features of the claimed subject matter, nor is it intended to limit the scope of the claimed subject matter.

BRIEF DESCRIPTION OF THE DRAWINGS

The following is a brief description of the drawings, which are presented for the purposes of illustrating the disclosure set forth herein and not for the purposes of limiting the same. A more complete understanding of the components, processes, and apparatuses disclosed herein can be obtained by reference to the accompanying figures. These figures are intended to demonstrate the present disclosure and are not intended to show relative sizes and dimensions or to limit the scope of the disclosed embodiments. Further, like reference numbers refer to like elements throughout.

FIG. 5 schematically depicts a side view of a continuous focal plane shift element having a surface with conical curvature, in accordance with some embodiments.

FIG. 6 schematically depicts a top view of the continuous focal plane shift element of FIG. 5.

FIG. 7 schematically depicts a side view of a continuous focal plane shift element having a surface with aspherical curvature, in accordance with some embodiments.

FIG. 8 schematically depicts a top view of the continuous focal plane shift element of FIG. 7.

FIG. 9 schematically depicts a side view of a discrete stepped focal plane shift element, in accordance with some embodiments.

FIG. 10 schematically depicts a top view of the discrete stepped focal plane shift element of FIG. 9.

FIG. 11 schematically depicts a side view of a continuous focal plane shift element having a surface with cylindrical curvature having a constant radius of curvature and a varying refractive index, in accordance with some embodiments.

FIG. 12 schematically depicts a top view of the continuous focal plane shift element of FIG. 11.

FIG. 13 schematically depicts an optical system with discrete multi-path focal plane shifting and lateral displacement of combined beam portions, in accordance with some embodiments.

FIG. 14 schematically depicts a y-z cross section for the first beam portion P1 and the second beam portion P2 for the optical system of FIG. 13.

DETAILED DESCRIPTION

As noted above, a fluidic processing system may include an optical system used for illuminating one or more flow-paths (e.g., to monitor, analyze or detect particles and/or liquids flowing in the flow-path(s)). In such a fluidic processing system, it may be beneficial to focus incident light on one or more individual flow-paths in one or more directions. A focusing element, such as a lens, a diffractive focusing element, a refractive focusing element or a reflective focusing element, may be used to focus an incident light beam on one or more flow-paths in a fluidic processing system. However, in many fluidic processing systems, the distance from the focusing element to a flow-path in the fluidic processing system (an optical path distance to the flow-path) may be different for different flow-paths. For example, a microfluidic chip that is not perpendicular to an incident light beam from a focusing element could result in different optical path distances from the focusing element to different flow-paths of the microfluidic chip. Thus, an incident beam that is focused in one or more dimensions for one flow-path may not be focused for another flow-path with a different optical path length from the focusing element. Some embodiments address this by producing a light beam simultaneously focused at two or more different distances along an optical path, which allows incident light from a single light source to be focused at two or more flow-paths having different optical path lengths from the focusing element.

Embodiments taught herein provide an optical system and one or more optical elements that focus an incident light beam to produce a light beam having different portions simultaneously focused at two or more different distances along an optical path. The optical system may be for illuminating flow-paths in a fluidic processing system, and may be particularly useful for illuminating flow-paths in a microfluidic system. Some embodiments provide a focal plane shift element configured to focus light incident on a first portion of the focal plane shift element to form a first beam portion focused to a first location a first distance from the focal plane shift element. The focal plane shift element is also configured to focus light incident on a second portion of the focal plane shift element to form a second beam focused to a second location at a second distance from the focal plane shift element.

Figure 1:
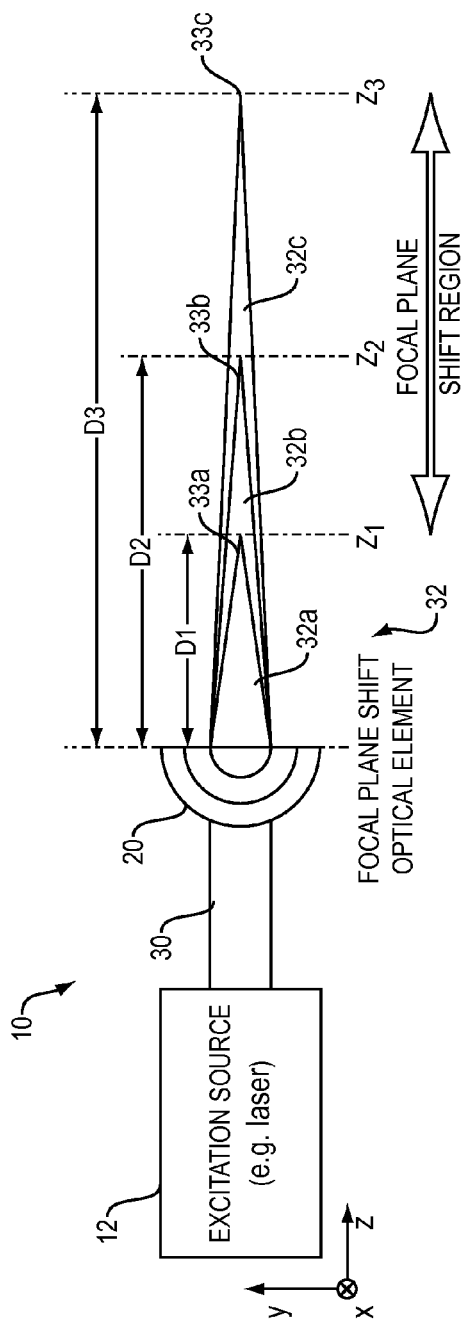
FIG. 1 schematically depicts a side view of an optical system including a continuous focal shift element, in accordance with some embodiments.
Figure 3:
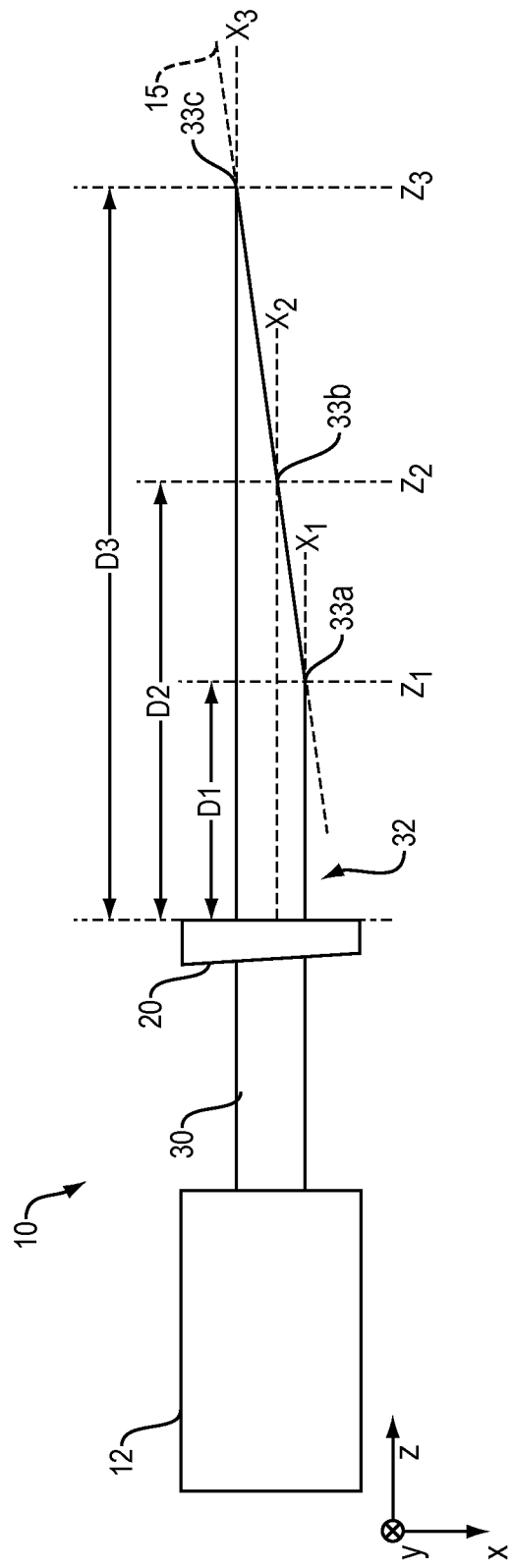
FIG. 3 schematically depicts a top view of the optical system of FIG. 1.

FIGS. 1 and 3 illustrate a first optical system 10 including a light source 12 for providing an incident light beam 30 and at least one optical element (e.g., continuous focal plane shift (FPS) element 20) configured to collect and focus the incident light beam 30 to produce a second light beam 32 having different portions simultaneously focused at two or more locations along an optical path. Second light beam 32 can theoretically be divided into an infinite number of portions corresponding to light incident on different lateral portions of the continuous FPS element 20 along the x-axis. For illustrative purposes, FIG. 1 shows three different portions (32a, 32b, 32c) of the second light beam 32 corresponding to light incident on three different lateral locations of the continuous FPS element 20, which focuses the light to three different locations (33a, 33b, 33c) on the gradient focal plane 15 (see also FIG. 3). As shown in FIGS. 1 and 3, each location (33a, 33b, 33c) is a different distance from the continuous FPS element 20. Beam portion 32a is focused in the y-direction to a location 33a in a plane $z_1$ that is a distance $D_1$ from the continuous FPS element 20 along the optical path. Portion 32b is focused in the y-direction to a location 33b in a plane $z_2$ that is a distance $D_2$ from the continuous FPS element 20 along the optical path. Portion 32c is focused in the y-direction to a location 33c in a plane $z_3$ that is a distance $D_3$ from the continuous FPS element 20 along the optical path. As shown in FIG. 3, locations 33a, 33b and 33c are also in the gradient focal plane 15.

Figure 2:
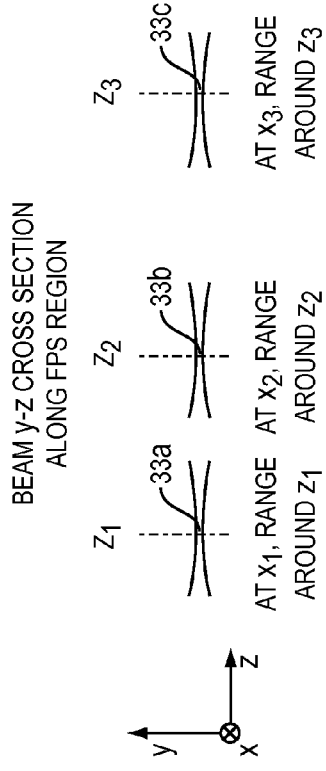
FIG. 2 schematically depicts y-z beam cross sections along the focal plane shift region of the optical system of FIG. 1.

FIG. 2 schematically depicts the cross section in the y-z plane of beam 32 at planes $z_1$, $z_2$, and $z_3$. The cross section of the focused beam is nearly identical at any given point in the gradient focal plane (e.g., at points $(x_1, z_1)$, $(x_2, z_2)$, and $(x_3, z_3)$). In general, the cross section would be the diffraction limit corresponding to the focal length of the corresponding portion of the continuous FPS element 20. In contrast, if a conventional lens was used, instead of a continuous FPS element, and the focal plane of the conventional lens was aligned to point $(x_2, z_2)$, the cross section of the beam at points $z_1$ and $(x_2, z_2)$ would be defocused.

Figure 4:
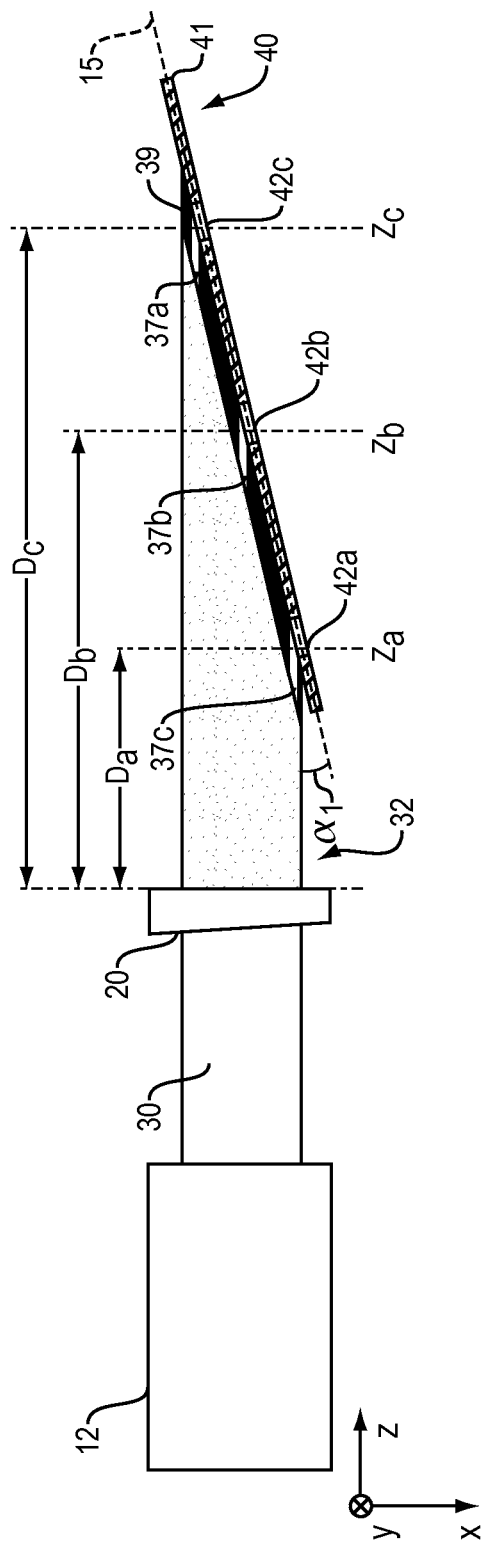
FIG. 4 schematically depicts a top view of a continuous focal plane shift element used to illuminate flow-paths, in accordance with some embodiments.

FIG. 4 is a top view of the incident beam 30, the continuous FPS element 20, and the second light beam 32 illuminating flow-paths 42a, 42b, 42c of a microfluidic system (e.g., microfluidic chip 40). As shown in FIG. 4, the continuous FPS element simultaneously focuses different portions of the beam 32 on three different flow-paths 42a, 42b, 42c, which are three different distances $D_a$, $D_b$, $D_c$ from the focal plane shift element 20.

As used herein, the term "light source" refers to any device for producing electromagnetic radiation. In exemplary embodiments, the light source 12 may be a laser, a diode laser, a monochromatic light source, a polychromatic light source, or any combination of the aforementioned. For example, the light source 12 may be a Coherent Sapphire 488/200 laser, which is a compact, air-cooled optically pumped semiconductor laser device producing about 200 mW of light at 488 nm, while the technology can also be used to produce light at other wavelengths. Alternatively, a diode pumped solid state (DPSS) laser may be used, which is capable of generating different wavelengths of light for excitation and/or illumination. The light source 12 may have a suitable wavelength for inducing fluorescence. One skilled in the art will recognize that any suitable light source may be used.

In some embodiments, portions of the beam 32 may pass through an optical mask 39 before reaching the flow-paths 42a, 42b, 42c. The optical mask 39 may define an array of apertures (e.g., pinholes 37a, 37b, 37c) with each aperture corresponding to a flow-path 42a, 42b, 42c.

As used herein, the term "fluidic processing system" refers to a system or device for handling, processing, ejecting and/or analyzing a fluid sample. The term "microfluidic system" refers to a fluidic processing system having microscale dimensions (i.e., less than 1 mm) and/or configured for processing droplets. Examples of a microfluidic system may include but are not limited to a droplet sorter or a microfluidic chip sorter, as described herein.

The term "flow-path," as used herein refers to any pathway that allows for the movement of fluids such as liquids and gases and any particles carried in the fluid. In some embodiments, a flow-path may be defined by a structural component such as a microchannel. In other embodiments, a flow-path may be defined by a path of a stream of fluid and/or particles with or without a corresponding structural component, for example, a path through a microchannel or a path of a jet of liquid or a jet of liquid that may break into a stream of droplets in a droplet sorter, respectively.

The term "microchannel" refers to a channel formed in or through a medium, for example, in a substrate such as a microfluidic chip, the channel having cross-sectional dimensions in the range between about 1.0 μm and about 1 mm. One of ordinary skill in the art will be able to determine an appropriate volume and length of a microchannel. The ranges are intended to include the above-recited values as upper or lower limits.

Flow-paths can have any selected shape or arrangement, examples of which include a linear or non-linear configuration and a U-shaped configuration. A microfluidic system, for example a microfluidic chip may comprise any suitable number of flow-paths for transporting fluids. Although microfluidic chip 40 includes three flow-paths in the cross-sectional view of FIG. 4, one of ordinary skill in the art will appreciate that microfluidic chip 40 may include more flow-paths or fewer flow-paths flowing through an area to be illuminated (e.g., 1, 2, 4, 8, 12, 24, 36, 72, 144, 288, etc.). In some embodiments, a microfluidic system may include a disposable cartridge defining one or more flow-paths external to a particle processing component, for example, external to a microfluidic chip. Flow-paths in a microfluidic system are not limited to being on the micro-fluidic scale.

For example, flow-path(s) may be defined by a closed channel system of capillary size in a cartridge.

A microfluidic chip may be any device or chip including microchannels for flowing a substance, such as particles (e.g., cells) therethrough. For example, the microfluidic chip may comprise a particle sorting system, such as the particle sorting systems described in U.S. Pat. No. 6,808,075, and U.S. Pat. No. 6,976,590, the contents of both patents are herein incorporated by reference in their entirety.

Other suitable microfluidic systems are described in U.S. Pat. No. 7,179,423, U.S. Patent Publication No. 2003-0015425 A1, U.S. Patent Publication No. 2002-0197733 A1, U.S. Pat. No. 7,211,442, U.S. Pat. No. 8,277,764, and U.S. Patent Publication No. 2012-0177902 A1, all of which are herein incorporated by reference in their entirety.

Other suitable microfluidic systems may have a plurality of nozzles associated with a plurality of flow-paths. The flow-paths may have closed portions (e.g., a channel upstream of a nozzle or in the nozzle) open portions (e.g., a pre-droplet in contact with the nozzle, a detached droplet in air, a jet in air, etc.). An optical system may illuminate closed portions of beam paths, open portions of beam paths, or both. Exemplary microfluidic systems including a plurality of nozzles appear in International Patent Application No. PCT/US2012/023247 filed Jan. 31, 2012, published as International Publication No. WO 2012/0106294 A1 on Jan. 31, 2012, which is incorporated by reference herein in its entirety.

Some embodiments may be employed in combination with various types of detectors and various types of optical systems. For example, U.S. Pat. No. 7,298,478, filed Aug. 9, 2004, which is incorporated by reference herein in its entirety, discloses optical detectors and optical systems that may be combined with embodiments described herein.

As used herein, the term "particle" refers to a discrete unit of matter. For example, particles may include atoms, ions, molecules, cells, agglomerates, or the like. Particles may also refer to (macro) molecular species such as proteins, enzymes, polynucleotides, or the like. Particles are typically between 10 nm and 1 mm in diameter. In some embodiments, particles are between 100 nm and 250 µm in diameter. In further embodiments, particles are between 1 µm and 30 µm in diameter. Particles may be naturally occurring or synthetic, or may combine natural and synthetic components within a single particle. Particles may refer to biological particles. For example, particles may include cells (for example, blood platelets, white blood cells, tumorous cells or embryonic cells, spermatozoa, to name a few), liposomes, proteoliposomes, yeast, bacteria, viruses, pollens, algae, or the like. Particles may also refer to non-biological particles. For example, particles may include metals, minerals, polymeric substances, glasses, ceramics, composites, or the like.

Various types of microfluidic systems (e.g., microfluidic chip 40) may be used in conjunction with exemplary embodiments. In the embodiment depicted in FIG. 4, the microfluidic chip 40 includes a substrate 41 in which the flow-paths 42a, 42b, 42c are disposed. The flow-paths 42a, 42b, 42c transport fluid and/or particles through the microfluidic chip 40 for processing, handling, and/or performing any suitable operation on a liquid sample (e.g., a particle sorting system). In some embodiments, the flow-paths 42a, 42b, 42c may be associated with a plurality of flow cytometers.

A microfluidic sorting system that employs exemplary optical systems and/or exemplary microfluidic chips may have a wide variety of applications as a therapeutic medical device enabling cell-based therapies, such as blood transfusion, bone marrow transplants and mobilized peripheral blood implants. Microfluidic sorting systems may be capable of selecting cells based on multiple surface and/or intracellular marker protocols, independent of protocols and necessary reagents. In exemplary embodiments, a microfluidic system may employ a closed, sterile, disposable cartridge including a microfluidic chip. The microfluidic system may process particles (e.g., cells) at high speeds, and deliver particles (e.g., cells) with high yield and high purity.

For continuous FPS element 20, a distance between the focal plane shift element and a location of a focus of a beam portion formed from light incident on a portion of focal plane shift element located at a lateral position (e.g., along the x-axis in FIG. 4) continuously varies with the lateral position of the portion of the continuous FPS element. For some embodiments, a surface with a laterally changing radius of curvature produces the continuous focal plane shift. For example, as shown in FIGS. 5 and 6, continuous FPS element 20 has a conically curved surface 22 with a radius of curvature that varies with lateral position. At a first end portion 24 of the continuous FPS element the surface 22 has a radius of curvature $R_1$, and at a second end portion 26 the surface 22 has a smaller radius of curvature $R_2$.

An FPS element need not have a surface with spherical, cylindrical or conical curvature. For example, FIGS. 7 and 8 schematically depict a side view and a top view, respectively, of a continuous FPS element 50 having a surface 52 with aspherical curvature (i.e., the surface does not have spherical curvature or cylindrical curvature).

An FPS element need not be a continuous FPS element. For example, FIGS. 9 and 10 schematically depict a discrete FPS element having different sections 64a-64e, each section having a surface 62a-62e with a different radius of curvature. For a discrete FPS element, a distance between the discrete FPS element and a location of a focus of a beam portion formed from light incident on a portion of the discrete FPS element located at a lateral position does not vary continuously with the lateral position of the portion of the discrete FPS element. Instead, a distance between the discrete FPS element (e.g., discrete FPS element 60) and a location of a focus of a beam portion formed from light incident on a section (e.g., sections 62a-62e) varies laterally in steps from section to section.

An FPS element need not have a surface with a varying radius of curvature. For example, FIGS. 11 and 12 schematically depict a side view and a top view, respectively, of a continuous FPS element 70 having a surface 72 with a constant radius of curvature. Continuous FPS element 70 has an index of refraction that continuously varies from a first value $n_1$ at a first end portion 74 to a second higher value $n_2$ at a second end portion 76. In other embodiments, a discrete FPS element may have multiple sections with each section having a different index of refraction.

Some embodiments include an optical system for illuminating flow-paths in a fluidic processing system that incorporates a focal plane shift element. Such an optical system may include a light source (e.g., light source 12 of FIGS. 1-2), and a continuous focal plane shift element (e.g., continuous FPS element 20 of FIGS. 1-2, continuous FPS element 50 of FIGS. 7 and 8, continuous FPS element 70 of FIGS. 11 and 12) or a discrete focal plane shift element (e.g., discrete FPS element 60 of FIGS. 9-10).

Although embodiments of the continuous FPS element and the discrete FPS element are described above in the context of illumination of flow-paths in a microfluidic system, one of ordinary skill in the art would recognize that continuous FPS elements and discrete FPS elements may be used for many other purposes in many other fields. For example, the focusing of light to multiple locations in biological applications such as parallel illumination of specimens on non-flow systems, (e.g., imaging and measuring optical characteristics of continuous samples such as tissue biopsies, or discrete samples, such as might be laid out over a glass slide substrate such as in microarrays, or in a multiwall/microtitre plate). Additional applications might include metrology and related industrial applications where multi-location measurements are required. Laser machining technologies and speed may also be improved by providing additional focused beams from a single source over a large area. Further applications may include entertainment, display or projection systems (e.g. heads-up displays) where the image presented to an observer is to be produced over a large area, or at an angle to an illumination source.

Some embodiments include an optical system for illuminating flow-paths in a fluidic processing system that includes beamsplitters to split the incident beam into multiple paths and at least one optical element in one or more of the multiple paths that introduce relative focal plane shift. For example, FIG. 13 illustrates an optical system 80 including a light source 82 providing an incident light beam 84. The optical system 80 further includes a beamsplitter 86 configured to divide the incident light beam 84 between different optical paths: a primary beam portion 88 traveling along a primary optical path P1, and a secondary beam portion 90 traveling along a focal shift optical path P2. The optical system 80 may further include reflective elements (e.g., mirrors 95, 99) for directing light along the focal shift optical path P2. The optical system 80 also includes a beam-combiner 92 configured to combine light from primary optical path P1 and light from focal shift optical path P2 into a composite beam 94 having a primary portion 94a, including from the primary optical path P1, and a secondary portion 94b, including light from the focal shift optical path P2.

The optical system 80 includes at least one optical element (e.g., lenses 96 and 98) in the focal shift optical path P2 configured to shift a focal plane F2 of the composite beam secondary portion 94b relative to a focal plane F1 of the composite beam primary portion 94a. The optical system 80 also includes at least one beam focusing element for primary optical path P1 (e.g., primary beam focusing lens 100) positioned before the beamsplitter 86 or after the beam-combiner 92. The at least one beam focusing element for primary optical path P1 (e.g., primary beam focusing lens 100) is configured to focus the composite beam primary portion 94a to a first location 102 at a first distance $D_{102}$ from the beam-combiner 92 thereby illuminating a first flow-path 106 of a microfluidic system (e.g., microfluidic chip 110). The at least one optical focusing element for primary optical path P1 (e.g., primary beam focusing lens 100) is further configured to, in combination with the at least one optical element for the focal shift optical path P2 (e.g., lenses 96 and 98), shift the focal plane of the composite beam secondary portion 94b to a second location 104 a second distance $D_{104}$ from the beam-combiner 92, thereby illuminating a second flow-path 108.

The optical elements for primary optical path P1 and focal shift optical path P2 may be refractive optical elements, diffractive optical elements, reflective optical elements, or any combination of the aforementioned. For example, the at least one second beam optical element may include a plano-convex refractive first lens 96 and a plano-convex refractive second lens 98 with a focal length equivalent to that of the first lens. The primary beam focusing lens 100 may be a plano-convex refractive lens.

FIG. 14 illustrates y-z beam cross sections for the first combined beam portion 94a (P1) and the second combined beam portion 94b (P2) through focal planes F1 and F2. As shown in FIG. 14, the first combined beam portion 94a is focused at, and has a minimum beam waist $W_1$ at, plane F1, but the second combined beam portion is relatively broad at plane F1. In contrast, the second combined beam portion 94b is focused at, and has a minimum beam waist $W_2$ at, plane F2.

Although FIG. 13 shows an optical system with a first beam path P1 and a second beam path P2, one of ordinary skill in the art, in view of the present disclosure, will recognize that embodiments may include optical systems with additional beam paths and additional beam path optical elements for further shifting a focal plane. Such embodiments would form additional combined beam portions simultaneously focused at different focal planes and could be used to illuminate additional flow-paths in a fluidic processing system.

Although FIG. 13 shows the first combined beam portion 94a laterally offset in the x-direction with respect to the second combined beam portion 94b, in other embodiments, the first combined beam portion may be laterally offset in the y-direction or in a combination of the x and y directions with respect to the second beam portion.

Figure 15:
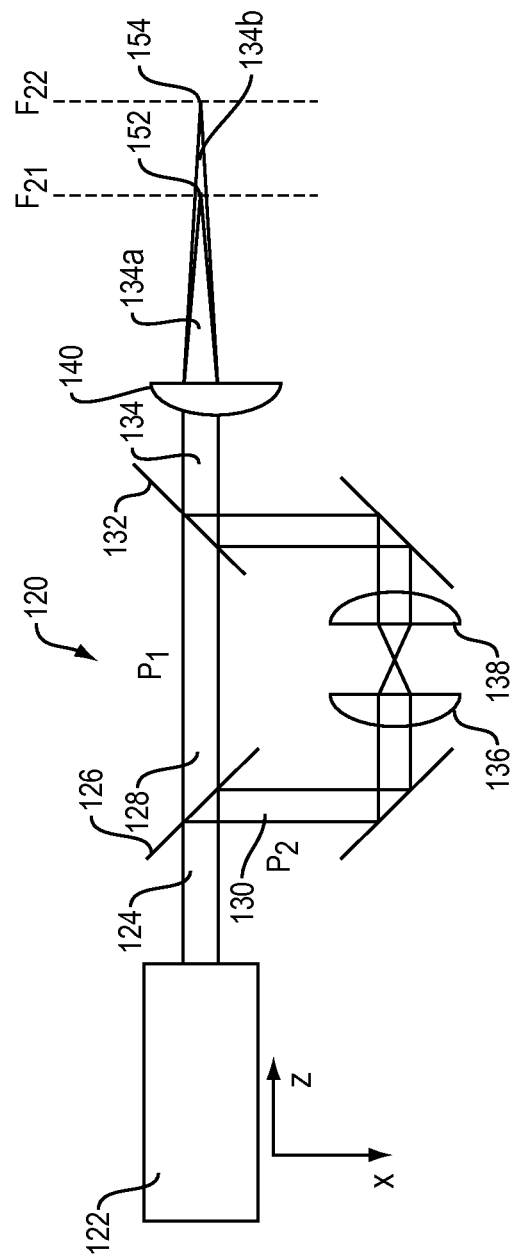
FIG. 15 schematically depicts another optical system with discrete multi-path focal plane shifting and no lateral displacement of the combined beam portions, in accordance with some embodiments.

In some embodiments, the second combined beam portion is not laterally offset from the first combined beam portion. For example, FIG. 15 schematically depicts an optical system 120 including a light source 122 that produces an incident beam 124. A beamsplitter 126 splits the incident beam 124 into a first beam portion 128 and a second beam portion 130. A beam-combiner 132 combines light 128 from a primary optical path P1 and light 130 from a focal shift optical path P2 to form a composite beam 134 having a primary portion 134a and a secondary portion 134b where the primary portion 134a is not laterally offset from the secondary portion 134b. At least one optical element (e.g., lenses 136, 138) is in the focal shift optical path P2. At least one optical element along the primary optical path P1 (e.g., focusing lens 140) focuses the composite beam primary portion 134a to a first location 152 in a first focal plane F21. The at least one optical element along the primary optical path P1 (e.g., focusing lens 140) in combination with the at least one optical element along the focal shift optical path P2 (e.g., lenses 136, 138) focuses the composite beam secondary portion 134b to a second location 154 in a second focal plane F22. Although location 152 and location 154 lie in different planes, they are not laterally offset. Such a system may be useful for providing uniform single line off-axis illumination of objects used in semiconductor inspection and processing, microfabrication, and/or brightfield/fluorescence imaging applications.

Figure 16:
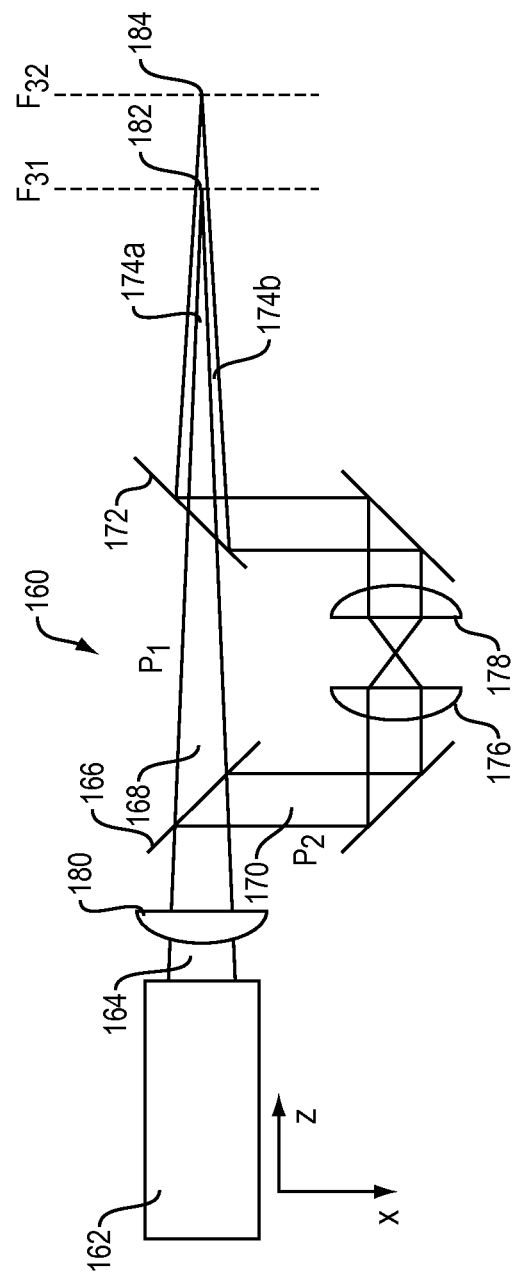
FIG. 16 schematically depicts another optical system with discrete multi-path focal plane shifting in which a focusing element is positioned before a beam splits into multiple paths, in accordance with some embodiments.

Although FIGS. 13 and 15 depict embodiments in which the one or more focusing optical elements of the primary optical path P1 (e.g., focusing lens 100 and focusing lens 140 respectively), are positioned after the beamsplitter and beam-combiner in the composite beam, in other embodiments, the one or more focusing optical elements of the primary optical path P1 may be positioned before the beamsplitter (e.g., in the incident beam). For example, FIG. 16 schematically depicts an optical system 160 including a light source 162 that produces an incident beam 164. The incident beam 164 is split by a beamsplitter 166 into a primary beam portion 168 along a primary optical path P1 and a secondary beam portion 170 along a focal shift optical path P2. Optical system 160 also includes one or more optical elements (e.g., lenses 176 and 178) along the focal shift optical path P2. A beam-combiner 172 combines light from the primary optical path P1 and the focal shift optical path P2 to form a composite beam including a primary portion 174a and a secondary portion 174b. Optical system 160 includes one or more optical elements (e.g., focusing lens 180) in the primary optical path P1 that focuses the composite beam primary portion 174a to a location 182 in a focal plane $F_{31}$. The one or more optical elements (e.g., focusing lens 180) in the primary optical path P1, in combination with the one or more optical elements (e.g., lenses 176 and 178) in the phase shift optical path P2, focuses the composite beam secondary portion 174b to a location 184 in a focal plane $F_{32}$.

Figure 18:
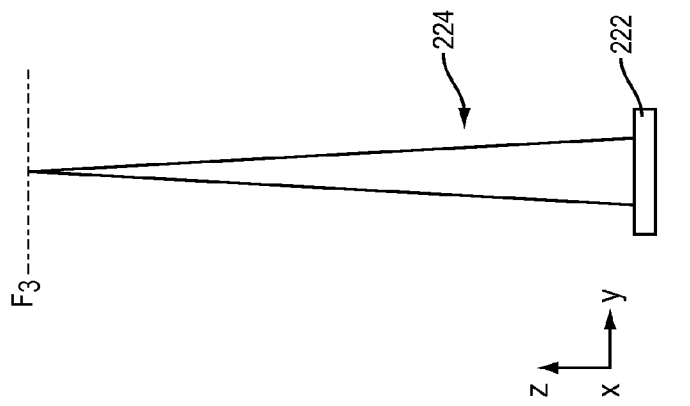
FIG. 18 schematically depicts a side view of the segmented mirror and segmented output beam of FIG. 17.
Figure 17:
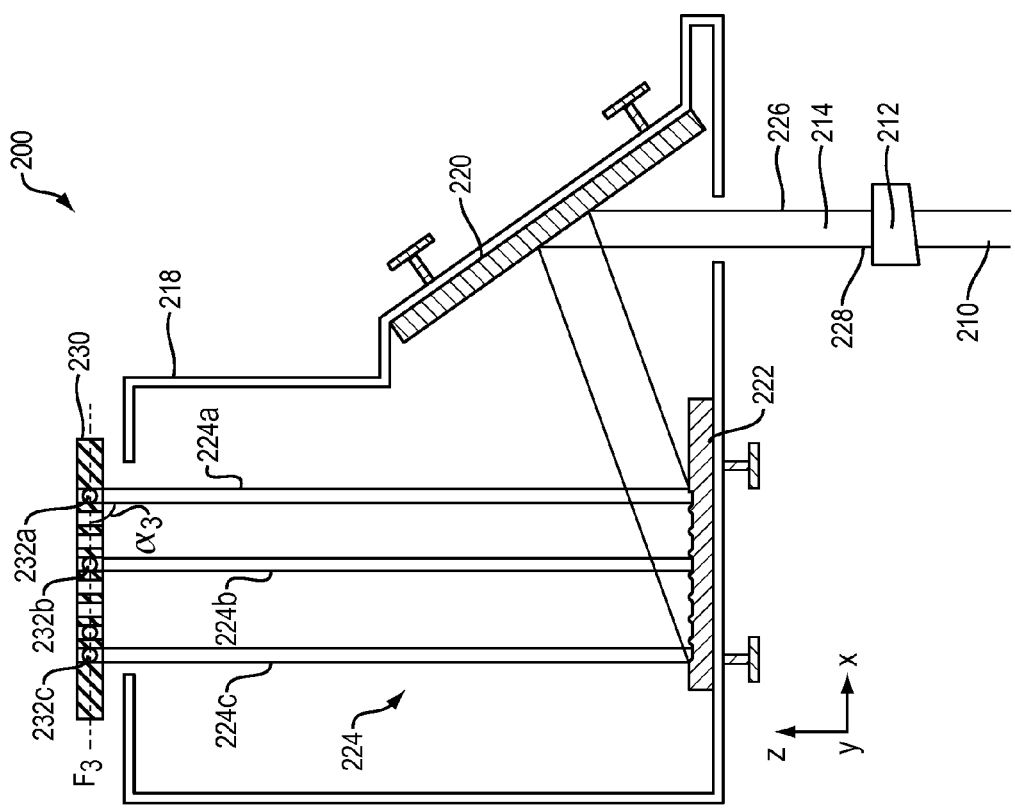
FIG. 17 schematically depicts an optical system including a continuous focal plane shift element and a segmented mirror, in accordance with some embodiments.

FIG. 17 schematically illustrates a system 200 in which a continuous focal plane shift element and a segmented mirror are employed to produce a segmented output beam with each segment focused on a flow-path of a fluidic processing system. FIG. 18 schematically depicts a side view of the segmented mirror and segmented reflected beam. As shown in FIG. 17, an incoming beam from a light source 210 is sent through a continuous FPS element 212. The incident beam 214 from the continuous FPS element 212 is directed into a segmentation column 218, which includes an incidence mirror 220 and a segmented mirror 222. The incident beam 214 is reflected off of the incidence mirror 220 and directed onto the segmented mirror 222. The segmented mirror 222 produces a segmented output beam 224 with portions 224a-224c focused at a focal plane F3. For clarity, only three portions of the segmented output beam 224 are depicted in FIG. 17. Although the portions of the segmented output beam 224a-224c are all focused at the same focal plane F3, each portion 224a-224c travels a different path distance from the continuous FPS element 212 to the focal plane F3. Portion 224a travels the shortest path 226 and portion 224c travels the longest path 228. The continuous FPS element 212 focuses the portions 224a-224c to the same focal plane F3 even though each portion travels a different distance from the continuous FPS element 212 to the focal plane F3. In some embodiments, each portion 224a-224c of the segmented output beam is focused to a flow-paths 232a-232c of a microfluidic system (e.g., microfluidic chip 230) to illuminate particles 240b, 240e, and/or fluids flowing through the flow-paths.

One of ordinary skill in the art, in view of the present disclosure, will recognize that in some embodiments, other optical elements may be included in an optical system. For example, beam shaping and/or beam conditioning optics (e.g., optical filters or other spectrally selective components, collimation lenses, etc.) may be included in an optical system. In embodiments including an FPS element, the beam shaping and beam conditioning optics may be positioned before the FPS element, after the FPS element or both. In embodiments including a beamsplitter and a beam-combiner, the beam shaping and beam conditioning optics may be positioned before the beamsplitter, after the beam-combiner, in one or more of the split be paths, or any combination of the aforementioned.

An incidence angle between incident beam portions and a plane of flow-paths in a fluidic processing system may vary in different embodiments. For example, in optical system 10 of FIG. 4 the incidence angle is acute angle $\alpha_1$, in optical system 80 of FIG. 13 the incidence angle is acute angle $\alpha_2$, and in optical system 200 of FIG. 17 the incidence angle is right angle $\alpha_3$. In other embodiments, the angle may be obtuse or have any other suitable value.

Some embodiments of the invention enable reliable simultaneous illumination of particles, particle streams and/or flows in a plurality of flow-paths by simultaneously focusing portions of the incident light on different flow-paths located at different optical beam path distances from one or more focusing elements. One of ordinary skill in the art will recognize that a focal plane shifted portion of the incident light need not be exactly focused at the flow-path for reliable imaging and or illumination. For example, in some embodiments, the focal plane corresponding to a particular flow-path may be slightly in front of or behind the location of a particle flowing along the flow-path, but still be sufficiently focused for imaging or illumination of the particle. Thus, in some embodiments, the focal plane shifted portion of the incident light corresponding to a particular flow-path may overlap with the flow-path or may be near the flow-path.

Although light sources are described above as providing an incident beam of light, in some embodiments, a light source may produce multiple incident beams of light. In some embodiments, a beam of light produced by a light source may be split into multiple beams at any point in the optical system.

Multiple different embodiments of focal plane shift (FPS) elements having different structures are depicted and described herein (e.g., continuous FPS element 20 of FIGS. 1, 3 and 4-6, continuous FPS element 50 of FIGS. 7 and 8, discrete FPS element 60 of FIGS. 9 and 10, and FPS element 70 of FIGS. 11 and 12). The claimed subject matter is not limited to particular structures for focal plane shift elements, or to embodiments depicted in particular figures.

The present invention has been described relative to illustrative embodiments. Because certain changes may be made in the above constructions without departing from the scope of the invention, it is intended that all matter contained in the above description or shown in the accompanying drawings be interpreted as illustrative and not in a limiting sense. For example, the illustrative embodiments have referenced fluidic processing systems and microfluidic systems. However, it is understood that the optical elements and optical systems described and claimed herein may be used with other systems, including non-fluidic systems.

It is also to be understood that the following claims are to cover all generic and specific features of the invention described herein, and all statements of the scope of the invention which, as a matter of language, might be said to fall therebetween.

The invention claimed is:

1. An optical system for illuminating a plurality of flow-paths in a fluidic processing system, the optical system comprising:
    a light source providing an incident first light beam; and
    at least one optical element configured to collect and simultaneously focus the incident first light beam to produce a second light beam having different portions focused at two or more different locations along an optical path downstream of the optical element, wherein the different locations have different distances along the optical path and different lateral positions across the optical path.

2. The optical system of claim 1, wherein the at least one optical element comprises a focal plane shift element configured to focus light incident on a first portion of the focal plane shift element at a first lateral position to form a first beam portion focused at a first location a first distance from the focal plane shift element thereby illuminating a first flow-path, and configured to focus light incident on a second portion of the focal plane shift element at a second lateral position to form a second beam portion focused at a second location a second distance from the focal plane shift element thereby illuminating a second flow-path.

3. The optical system of claim 2, wherein the first location at least partially overlaps with the first flow-path and wherein the second location at least partially overlaps with the second flow-path.

4. The optical system of claim 2, wherein the first location is near the first flow-path and wherein the second location is near the second flow-path.

5. The optical system of claim 2, wherein a distance between the focal plane shift element and a location of a focus of a beam portion formed from light incident on a portion of focal plane shift element located at a lateral position varies with the lateral position of the portion of the focal plane shift element.

6. The optical system of claim 2, wherein a distance between the focal plane shift element and a location of a focus of a beam portion formed from light incident on a portion of focal plane shift element located at a lateral position continuously varies with the lateral position of the portion of the focal plane shift element.

7. The optical system of claim 2, wherein the focal plane shift element is a refractive element.

8. The optical system of claim 7, wherein the focal plane shift element has a laterally varying index of refraction.

9. The optical system of claim 2, wherein the focal plane shift element includes a surface having a laterally varying radius of curvature.

10. The optical system of claim 2, wherein the focal place shift element is a diffractive element.

11. The optical system of claim 1, wherein the at least one optical element comprises:
    a beamsplitter configured to divide the incident first light beam into a first beam portion and a second beam portion;
    at least one second beam optical element set in a path of the second beam portion;
    a beam-combiner configured to combine the first beam portion and the second beam portion into a combined beam; and
    a primary beam focusing element positioned before the beamsplitter or after the beam-combiner and configured to focus the first beam portion of the combined beam to a first location at a first optical path distance from the primary beam focusing element thereby illuminating a first flow-path, and configured to, in combination with the lens set, focus the second beam portion of the combined beam to a second location a second optical path distance from the primary beam focusing element thereby illuminating a second flow-path.

12. The optical system of claim 11, wherein the primary beam focusing element is positioned in the optical path before the beamsplitter.

13. The optical system of claim 11, wherein the primary beam focusing element is positioned in the optical path after the beam-combiner.

14. The optical system of claim 11, wherein the optical system is configured such that the first beam portion of the combined beam is laterally offset from the second beam portion of the combined beam.

15. The optical system of claim 1, wherein each of the two or more different locations along the optical path correspond to a different flow-path of a microfluidic system.

16. An optical system for illuminating flow-paths in a fluidic processing system comprising:
    a light source providing an incident light beam; and
    at least one optical element configured to collect and simultaneously focus the incident light beam forming image planes located at two or more different distances along an optical path downstream of the optical element and at two or more different lateral positions across the optical path.

17. The optical system of claim 16, wherein the at least one optical element comprises a focal plane shift element configured to focus light from a first portion of the focal plane shift element at a first lateral position forming a first image at a first distance from the focal plane shift element thereby illuminating a first flow-path, and configured to focus light from a second portion of the focal plane shift element at a second lateral position forming a second image at a second distance from the focal plane shift element thereby illuminating a second flow-path.

18. The optical system of claim 17, wherein a distance between the focal plane shift element and an image formed from light incident on a portion of focal plane shift element located at a lateral position varies with the lateral position of the portion of the focal plane shift element.

19. The optical system of claim 17, wherein a distance between the focal plane shift element and an image formed from light incident on a portion of focal plane shift element located at a lateral position continuously varies with the lateral position of the portion of the focal plane shift element.

20. The optical system of claim 16, wherein each image plane is located at a different flow-path of a microfluidic system.

21. The optical system of claim 16, wherein each image plane is located near a different flow-path of a microfluidic system.

22. An optical system for illuminating a plurality of flow-paths in a fluidic processing system, the optical system comprising:
    a light source providing an incident first light beam;
    at least a first optical element configured to collect and focus at least a first portion of the incident first light beam to produce a first light beam portion focused at a first location along an optical path; and
    at least a second optical element configured to collect and focus at least a second portion of the incident first light beam to produce a second light beam portion focused at a second location along the optical path,
    wherein the first location is different from the second location in both a downstream direction and a lateral direction, and
    wherein the first and second locations are downstream of both the first and second optical elements.

* * * * *